United States Patent [19]

Horton, Jr. et al.

[11] Patent Number: 5,168,514
[45] Date of Patent: Dec. 1, 1992

[54] MODULAR RADIOTHERAPY TREATMENT CHAIR AND METHODS OF TREATMENT

[75] Inventors: John L. Horton, Jr.; Robert C. Goga, both of Houston, Tex.

[73] Assignee: Board of Regents, The University of Texas System, Austin, Tex.

[21] Appl. No.: 766,758

[22] Filed: Sep. 27, 1991

[51] Int. Cl.$^5$ .................................................. A61B 6/04
[52] U.S. Cl. ..................................... 378/209; 378/68; 378/208; 297/136; 297/195
[58] Field of Search ............... 378/209, 208, 204, 195, 378/177, 178, 180, 68, 20, 64, 65; 297/135, 136, 138, 195

[56] References Cited

U.S. PATENT DOCUMENTS

| | | | |
|---|---|---|---|
| 1,294,300 | 11/1919 | Noel, Sr. | 297/138 |
| 3,655,967 | 4/1972 | Finkenzeller et al. | |
| 3,655,968 | 4/1972 | Moore et al. | |
| 4,064,401 | 12/1977 | Marden | 378/208 |
| 4,071,231 | 1/1978 | Kok | |
| 4,153,841 | 5/1979 | Kok | |
| 4,575,064 | 3/1986 | Menor | 378/209 |
| 4,699,425 | 10/1987 | Ohlson | |
| 4,896,917 | 1/1990 | Enevoldson | |
| 4,941,709 | 7/1990 | Kullvägen | |

FOREIGN PATENT DOCUMENTS 3-002584  1/1991  Japan ................................... 378/208

OTHER PUBLICATIONS

An isocentric chair for the simulation and treatment of radiation therapy patients, R. W. Miller et al., National Cancer Institute, Bethesda, Md. (no date).
The Structure of Radiation Oncology Practices in the Continental United States, James J. Diamond et al., Int. J. Radiation Oncology, Biol. Phys., vol. 14, p. 547 (1988).
A versatile radiotherapy treatment chair, C. J. Karzmark et al., British Journal of Radiology, vol. 53, p. 1190 (1980).
Artifice De Technique Dans L'Irradiation Au Bétatron, Journal de Radiologie et d'Electrologie, vol. 52, p. 189 (1971).
A radiotherapy treatment chair, G. A. Watson et al., British Journal of Radiology, vol. 44, p. 317 (1971).
Adjustable chair for radiotherapy of head and neck cancer, J. W. Boag et al., British Journal of Radiology, vol. 44, p. 316 (1971).
A New Radiotherapy Treatment Chair, George Wiernik, British Journal of Radiology, vol. 34, p. 676 (1961).
Preliminary Report on the Clinical Use of the Medical Research Council 8 MeV Linear Accelerator, R. Morrison et al., British Journal of Radiology, vol. 29, p. 177 (1956).
Patterns of Change in the Physics & Technical Support of Radiation Therapy in the USA 1975-1986, Chu et al., Int. J. Radiation Oncology Biol. Phys., vol. 17, p. 437 (1989).

*Primary Examiner*—David P. Porta
*Attorney, Agent, or Firm*—Arnold, White & Durkee

[57] ABSTRACT

A lightweight, modular radiotherapy treatment chair has a saddle-like seat for unobstructively supporting a patient in a stable and reproducible "straddled stance", allowing ample access to the patient, particularly improved access to the lower abdominal and pelvic regions, during treatment with therapeutic radiation. The chair attaches to a conventional isocentrically mounted radiotherapy treatment table or simulator to enable precise translational and rotational positioning of the patient. An optional frame may be used to secure selected immobilization devices, such as bite-blocks, head rests, and thermoplastic positioning aids, to further support and immobilize the patient during treatment. A method for treating malignant tumors present throughout various anatomical regions of a patient's body includes unobstructively supporting the patient in a straddled stance so that the tumor, or a plurality of tumors, can be treated with predetermined dosages of therapeutic radiation.

29 Claims, 3 Drawing Sheets

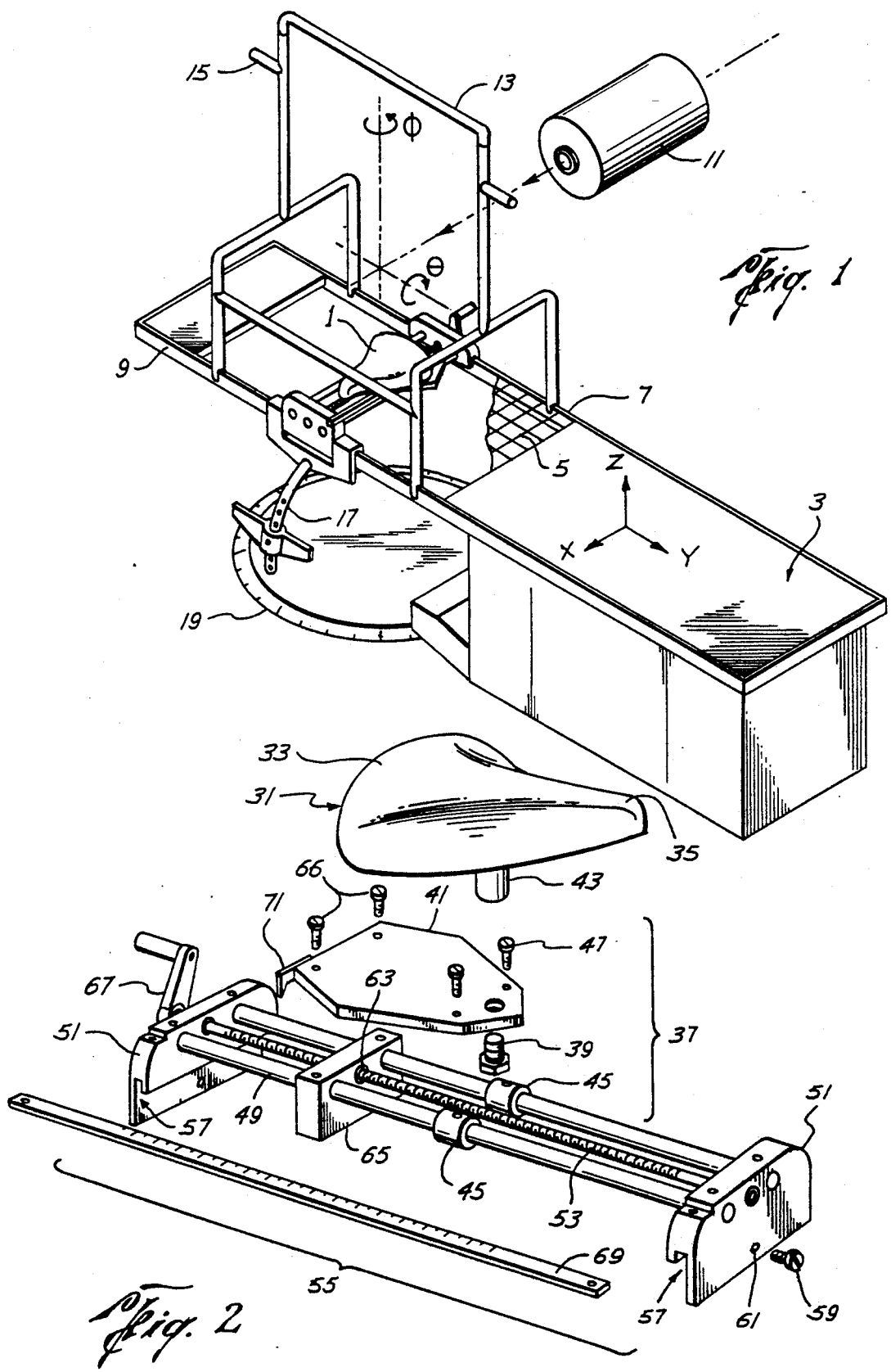

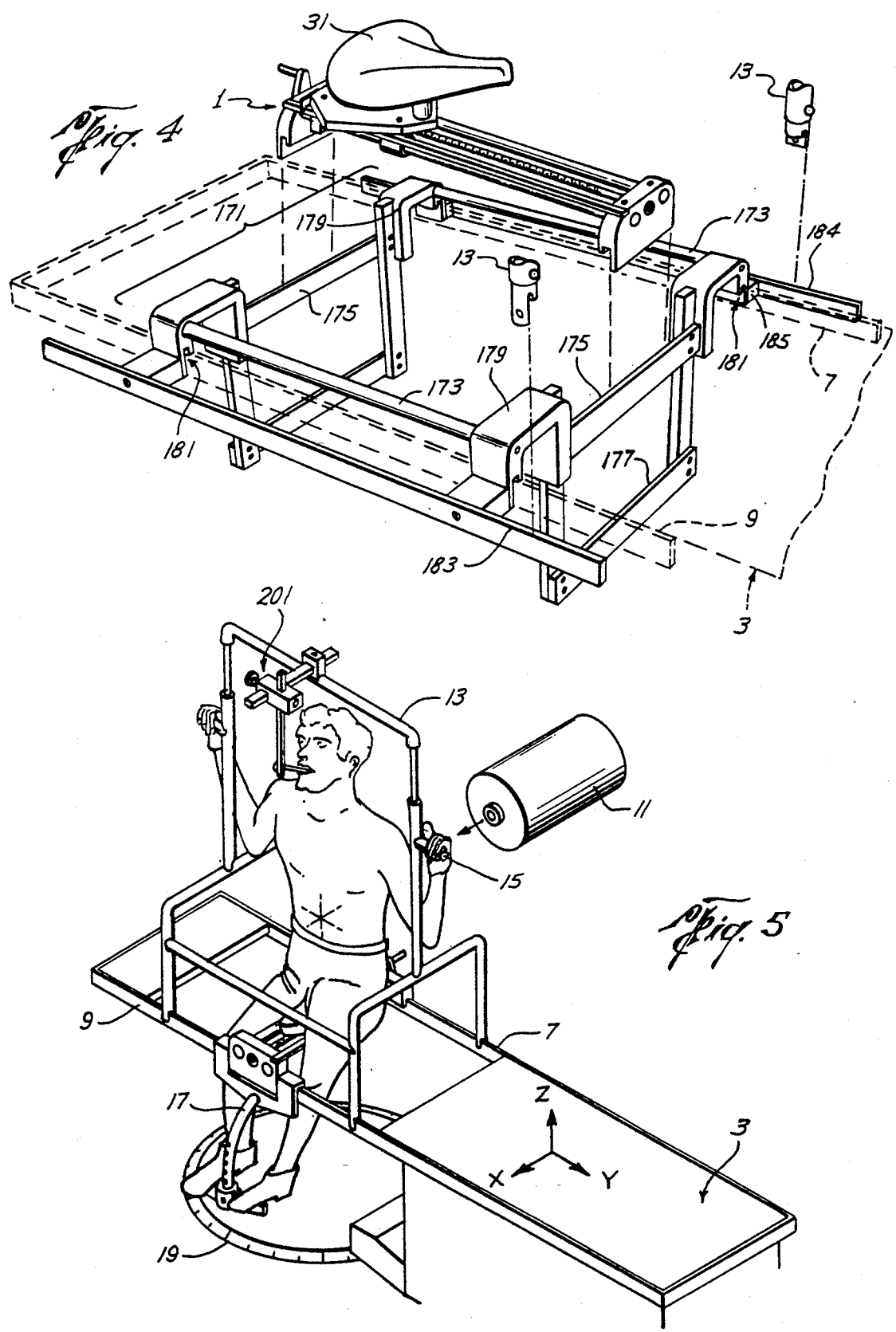

MODULAR RADIOTHERAPY TREATMENT CHAIR AND METHODS OF TREATMENT

BACKGROUND OF THE INVENTION

The present invention relates to a new method and apparatus for simulating and treating malignant tumors and, especially, multiple malignant tumors present throughout a patient's body. Specifically, the invention permits a number of anatomical regions, including the head, neck, thorax, abdominal and pelvic cavities, and some lower extremity areas, to be treated with beams of precision directed, therapeutic radiation while the patient remains comfortably supported in the same upright position.

Modern radiation therapy is an effective modality for treating various carcinomic diseases. More than one-half of all cancer patients in the United States receive some form of curative or palliative radiation treatment, with approximately 500,000 patients being treated annually. The majority of patients receiving external beam radiation therapy are treated on an isocentrically mounted treatment table, or patient support assembly (PSA), provided as standard equipment on most current accelerators and cobalt teletherapy treatment machines. In such systems, the radiation source is mounted on a gantry which rotates around a prone or supine patient. This method provides flexibility in setup and comfort for most patients, however, there are a variety of clinical situations in which patients can benefit from being treated in an upright sitting position.

Many patients, for example those who have carcinoma of the bronchus, superior vena cava syndrome, or malignant pleural effusions, often complain of dyspnoea (shortness of breath) of sufficient degree to make lying flat difficult or sometimes impossible. Children, especially, do not tolerate the recumbent position easily. For other patients who have varying degrees of dyspnoea, but who can manage to lay flat for short periods of time, treatment in the sitting position is often more comfortable. Patients having excess salivation, severe kyphosis and those with head and neck malignancies whose shoulders must be depressed in order to exclude them from the treatment fields are also better treated in a sitting position.

Patients with large mediastinal masses, e.g. Hodgkin's Disease, may preferably be treated in the sitting position. Mediastinal tumors often widen in the recumbent position, resulting in the irradiation of a larger volume of normal underlying lung. With patients seated upright, the effect of gravity on the tumor mass tends to elongate the disease, thus minimizing its frontal profile mass. The amount of lung which can be shielded in this position is appreciably greater than when the patient is lying down, thus greatly decreasing the morbidity of the treatment.

Hodgkin's patients with large breasts receiving mantle irradiation may likewise benefit from treatment in a sitting position. In the recumbent position, the breast tends to intrude into the axillary regions and, thus, may receive undesirable radiation exposure during treatment of the axilla. In the sitting position, however, the breast tends to fall away from the axillary regions and is, thus, more easily shielded. Similarly, other patients with large breasts, receiving irradiation for breast cancers, have been found difficult to treat in the supine position since the breasts tend to spread out over a larger area than one would like to encompass in the treatment fields. In the seated position the breasts can be more easily contained to the required area and may be provided with some support underneath.

The sitting position is also desirable for treating brain tumors in that it allows the head to be supported using bite-block or other unobstructive immobilization techniques so as to improve access to the head. See C. Karzmark, et al., *Br. J. Radiol.*, 53:926-28 (1975). With the patient supported in this manner, any portion of the brain, or indeed any tumor in the head or neck, can be easily treated with therapeutic radiation.

Despite the benefits to be gained from treating patients in a seated upright position, the technique does present certain difficulties. In order to minimize exposure of healthy tissue to high level dosages of radiation, for instance, modern radiotherapy treatment utilizes multiple beams of sharply collimated, high-energy radiation which are directed to intersect the tumor site at various angles. In this manner the volume of normal tissue raised to full tumor dosage can be restricted to an area immediately surrounding the geometrical limits of the malignant tissue (although a larger volume of normal tissue is irradiated to a lower dosage). Multiple portals are often used in combination with extensive field shaping and beam modification devices to achieve optimal dose distribution throughout the tumor. Working with these sharply collimated beams of high energy radiation calls for great accuracy in tumor localization, in beam directing, and in the setting up and restraining of the patient, especially when the tumor site is located in or near vital organs. Moreover, radiotherapy treatment is seldom accomplished in a single session, and usually requires several treatment sessions conducted over a period of time ranging from a few weeks to a few months. In order to ensure consistent results, it is necessary to accurately duplicate the treatment setup during each subsequent session.

Unfortunately, the development of precision treatment chairs with special features for executing sophisticated treatment plans has lagged behind that of treatment tables. The earliest radiotherapy treatment chairs consisted of little more than a flat sitting surface supported by a hydraulic pump and piston. Various support devices, such as adjustable back rests, headrests, and chin-rests, could be attached to the chair as needed to help support the patient in an upright position. The whole assembly was typically mounted on ball-castors so that the patient could be moved in a horizontal plane and rotated for placement in the radiation field. See, e.g., G. Wiernick, *Br. J. Radiol.*, 34:676-78 (1961); Y. Allain et al., *J. de Radiol. et d'Electrol.*, 52:189-92 (1971); and G. Watson et al., *Br. J. Radiol.*, 44:317-19 (1971). Although this design provided adequate mobility for positioning the patient in the radiation field, precise tumor localization was not possible due to the inherent limitations of the ball-castors. Because the force required to overcome static friction in the ball-castors is greater than the corresponding dynamic friction force, a sling-shot effect is created making precision adjustment of the chair exceedingly difficult.

Other radiotherapy chair designs, although capable of precision adjustment, lacked the repeatability necessary to efficiently execute multiple treatment sessions. A chair developed by Boag and Hodt, for instance, provided precision translational adjustment to a maximum of 5 cm from a selected central position. The chair itself was free to move on ball-castors and could be secured on the treatment floor by three locking pads. Once the chair was secured, the seat portion could be precisely adjusted in the radiation field for tumor localization. Rotation was accomplished by locking the rear pad and using it as the axis of rotation. The location of the chair on the treatment floor, however, was not easily duplicated during subsequent treatment sessions See, J. Boag and H. Hodt, *Br. J. Radiol.*, 44:316-17 (1971).

Another difficulty encountered in treating patients in the seated position is that the amount of physical structure required to support a patient in an upright position often obstructs or, at best, substantially reduces access to certain anatomical regions, especially the lower abdominal and pelvic cavities, which may require treatment. For example, a chair designed by Morrison et al. utilized an attachable back support and footrest assembly to convert a custom treatment table into a chair-like support. The positioning capability of the table itself provided adequate translational and rotational adjustment necessary for precise tumor localization. But, the additional back support structure blocked posterior fields and the table obstructed treatment of the pelvic and lower abdominal cavities, making the table inconvenient for general clinical use. See R. Morrison et al., *Br. J. Radiol.*, 29:177-86 (1956).

Miller et al. describes a free-standing isocentric chair for simulation and treatment of radiation therapy patients. The chair consists of three distinct components: a base-plate, a translation/elevation mechanism, and a seat. Rotation is provided by a centrally mounted turntable supported by specially constructed ball bearings. Vertical motion is provided by a scissors-type mechanism, in combination with a spring-loaded supplemental booster at the low end of travel. The seat consists simply of a rectangular aluminum plate having four attachment points, one on each corner. The seat is apparently designed to function as a "tool platform" for receiving various standard and customized patient support and immobilization devices. Adjustable lateral "restrictors" are used to center the patient on the seat, at the hips. Although the chair may provide ample mobility and adjustment capability, the extensive support structure, particularly the large rectangular seat and lateral restrictors, blocks access to the pelvic and lower abdominal cavities which may require treatment. See R. Miller et al., *Int'l. J. Rad. Onc. Biol. Phys.*, 2:464-473 (1991). The seat consists simply of a rectangular aluminum plate having four attachment points, one on each corner.

Varian Associates, Radiation Division, Palo Alto, CA, currently manufactures a treatment chair for optional attachment to its own radiotherapy treatment table design. The Varian chair is relatively simple in that it utilizes the horizontal, vertical, and rotational motions of the treatment table for precise tumor localization. The seat, foot-rest, arm-rests, head holder and bite-block are all supported by a central column which attaches to and extends up from the end of the treatment table. Unfortunately, this central column blocks beam access from behind the patient, making posterior treatment virtually impossible to administer. See, Varian Radiotherapy Accessories Catalog: Radiotherapy Treatment Chair, Varian Associates, Radiation Division, Palo Alto, CA., 94303.

The equipment heretofore available for treating patients in an upright position has been heavy, difficult to handle, and expensive. One of the more sophisticated radiotherapy treatment chairs, for example, is that designed by Karzmark et al. This chair, designed primarily for treating head and neck tumors, incorporates two axes of rotation in addition to longitudinal and lateral translation. A rotating turntable supports an x-y translation mechanism to which is attached a central support column. The seat, armrests, head support, and bite-block, attach to the central support column which can also rotate about its central axis. All adjustments are motor driven, using a remote pendant. The mechanical equipment and motors are installed beneath the floor in order to keep the height of the chair below a non-isocentrically mounted radiation source. Vertical adjustment is accomplished by adjusting the height of the radiation source. The substantial size and weight of the chair, however, prevents easy substitution of a treatment table when treatment in the supine position is required. See C. Karzmark et al., *Br. J. Radiol.*, 53:1190-94 (1980). Similarly, the Varian chair, described above, weighs over 150 pounds, also making it less than ideal for clinical use. Not only is the chair unwieldy, but its weight, in combination with that of the patient, can overstress the motors which operate the treatment table.

Simulation is an important step in planning and verifying a patient's treatment fields prior to initiating radiotherapy. The simulator is typically configured to emulate the final treatment setup, except that low-energy radiation is used to obtain a radiograph or tomograph of the tumor site. Ideally a single chair could be used to support a patient during both simulation and treatment. This permits simulation of the therapy to be performed with the patient in the same position as during the therapy, which is important because of the above-mentioned anatomical changes.

There remains a current need for a lightweight and inexpensive radiotherapy treatment chair that can be used in combination with existing radiotherapy treatment machines and simulators to unobstructively support a patient in a stable and reproducible upright position during treatment with therapeutic radiation.

SUMMARY OF THE INVENTION

The present invention provides a lightweight modular radiotherapy treatment chair that easily attaches to the side rails or frame of a conventional radiotherapy treatment table to support a patient in a stable upright position during radiotherapy treatment and simulation. The chair is designed to be inexpensive, taking advantage of the "tennis racket" opening and mechanized features of a standard radiotherapy treatment table. It is also designed to provide ease of use in a clinical setting. No piece of the unit weighs more than 20 pounds, and it is easily assembled on an open-couch type radiotherapy treatment table with a removable section (hereinafter referred to as a "table"). Modular construction makes the chair suitable for use with a variety of radiotherapy treatment tables with minimal modification and also makes it lightweight and easy to handle and assemble.

The chair includes a saddle-like seat for accurately locating the patient in the radiation field and providing unobstructive support during radiotherapy treatment. The seat is adapted to position the patient in a "straddled stance" in which the patient is supported upright with the legs extending substantially downward from the pelvis. This position provides excellent access to the patient, permitting numerous anatomical regions to be treated while the patient remains comfortably supported in the same position. An optional frame attaches to the treatment table for mounting a variety of selected support and immobilization devices, to provide additional support as needed.

The patient's position relative to the isocenter of the treatment machine or simulator is adjusted by horizontal and vertical positioning of the treatment table. The chair may be positioned on the treatment table, either parallel or perpendicular to its axis of elongation, for treating the patient with AP/PA fields or lateral fields, respectively. Oblique angles are achieved by rotating the base of the treatment table. Optional chair adjustments are provided for comfortably positioning the patient relative to the treatment table.

The present invention also provides a lightweight modular frame on which various positioning and immobilization devices may be attached to support a patient in an upright position on the chair. The frame is preferably adjustable to work with a variety of standard treatment machines and simulators and to provide flexibility in setup. The various adjustable components may be locked into position with, e.g., pins inserted through corresponding holes in adjacent components. Optional millimeter and angle scales may be provided for recording and reproducing all adjustments, including the position of selected immobilization devices, to enable accurate duplication of the complete setup during subsequent treatment sessions. An optional, separately adjustable footrest and a headrest may be used to provide additional support to the patient's legs and head, respectively, during treatment.

The present invention further provides an improved method for treating malignant tumors, and especially multiple malignant tumors present in the head, neck, thorax, abdominal and pelvic cavities. After a tumor is located and its approximate size and shape determined, the patient is supported in a straddled stance with the legs extending substantially downward from the pelvis. In this manner, any tumor site from the head to the pelvis, inclusive, can be irradiated using an isocentrically mounted radiation source. For multiple tumors, each site may be irradiated in succession while the patient assumes the same position for each series of exposures. This improves field matching capabilities in adjacent sites, such as head and neck, and reduces setup time for each treatment session.

The method according to the present invention is particularly useful for treating patients with malignant lymphoma involving lymph nodes of the upper torso, abdomen, and pelvis, because the legs extend downward from the pelvis allowing ample access to the mantle, abdominal and pelvic areas, which can be treated sequentially. Optionally, the treatment fields may be simulated prior to treatment using an appropriately selected simulator with the patient supported in a reproducible straddled stance using the treatment chair of this invention.

The present invention therefore provides an improved device for reproducibly supporting and immobilizing a cancer patient undergoing radiation therapy. This device provides unobstructed access to the entire torso, neck and head of the patient who is supported in an upright position. The present invention further provides a method for providing radiotherapy treatment using the device, which facilities accurate field matching and sequential treatment of multiple tumor sites without re-positioning the patient. These and other advantages of the present invention will be further appreciated from the drawings and from the detailed description provided below.

BRIEF DESCRIPTION OF THE DRAWINGS

So that the manner in which the herein described advantages and features of the present invention, as well as others which will become apparent, are attained and can be understood in detail, more particular description of the invention summarized above may be had by reference to the embodiment thereof which is illustrated in the appended drawings, which drawings form a part of this specification.

It is to be noted, however, that the appended drawings illustrate only exemplary embodiments of the invention and are therefore not to be considered limiting of its scope, for the invention may admit to other equally effective embodiments.

FIG. 1 is a perspective view of one embodiment of a radiotherapy treatment chair in accordance with the present invention;

FIG. 2 is a partially disassembled perspective view of the seat assembly of the present invention;

FIG. 4 is a partially disassembled perspective view of an optional support adaptor in accordance with the present invention;

FIG. 5 illustrates a patient supported in a device according to this invention a "straddled stance" for receiving therapeutic radiation according to the method of this invention.

DETAILED DESCRIPTION OF THE INVENTION

Figure 3:
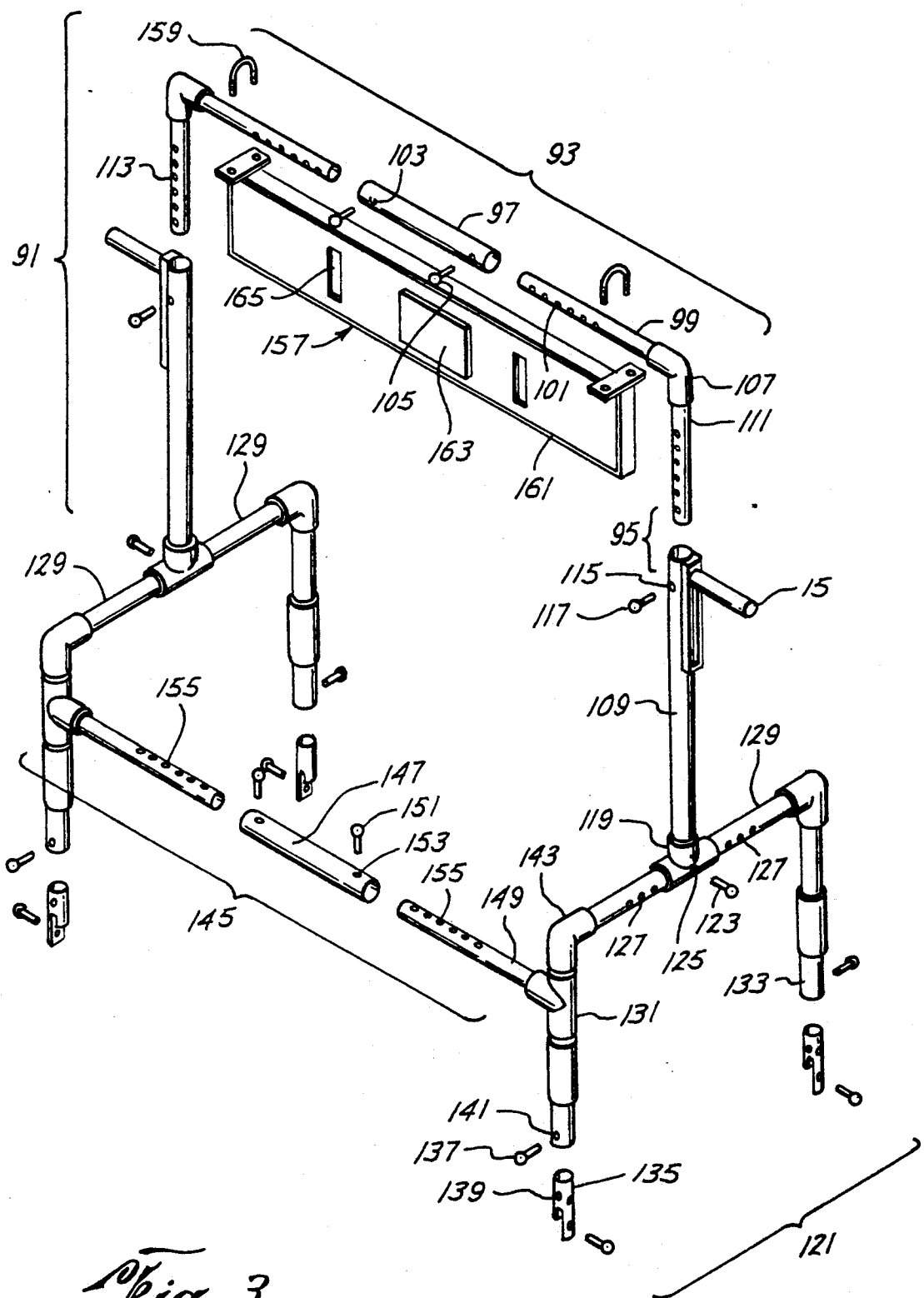
FIG. 3 is a partially disassembled perspective view of a frame in accordance with the present invention.

FIG. 1 shows one embodiment of a radiotherapy treatment chair in accordance with the present invention. The chair includes a seat assembly 1 which is adapted to span the "tennis racquet" opening or aperture of a standard open couch-type radiotherapy treatment table 3, formed by removing mesh support 5. In the configuration shown, seat assembly 1 is attachable between opposing side rails 7 and 9, which form the periphery of the aperture, to treat a patient with AP/PA fields emitted from radiation source 11. Alternatively, a support adaptor (discussed later in connection with FIG. 4) may be used to mount seat assembly 1 parallel to the axis of elongation of table 3 for treatment of a patient with lateral fields.

A preferred embodiment comprises optional frame 13, which is attachable in a variety of orientations between side rails 7 and 9 for treatment of a patient with AP/PA or lateral fields emitted from radiation source 11. With a patient supported on seat assembly 1, various immobilization devices, such as optional hand grips 15, may be attached to frame 13 in order to support and restrain the patient from undesirable movement during treatment. An optional footrest 17 similarly attaches to either side rail 7 or 9, using hooks or other means, for supporting a patient's feet and legs during treatment.

Treatment table 3 is, preferably, capable of precision translational motion in each of the X-Y-Z axes. It is mounted on a turntable 19, which is adapted to rotate about a vertical axis ($\phi$), which intersects a horizontal isocentric rotation axis ($\theta$) about which radiation source 11 is rotatable. The intersection of these two axes defines an isocenter through which radiation emitted from source 11 must pass. Rotation of radiation source 11 is accomplished by a gantry (not shown) which, typically, is capable of full 360° rotation about isocentric rotation axis (θ). Using this configuration, the patient may be treated in an upright position, sitting on seat assembly 1 and supported by frame 13.

Frame 13 and seat assembly 1 are both preferably adjustable to accommodate a variety of standard size radiotherapy treatment and simulation tables 3. The chair, according to this invention, is currently being used on an Oldelft simulator and a Varian Extended-Travel-Range couch. In combination with these machines, the chair of the present invention enables simulation and treatment of malignant disease present in any site from the head and neck to the pelvis, inclusive, as well as some lower extremity areas, using the same chair position. Alternatively, mesh support 5 may be replaced on table 3 to enable simulation and treatment in a recumbent position. Setup of the treatment table and chair is substantially the same as shown in FIG. 1 when used with a radiographic simulator.

FIG. 2 is a partially disassembled perspective view of seat assembly 1 of FIG. 1. A saddle-like seat 31 has a contoured upper surface defining a cantle 33 and a pommel 35. The size and shape of seat 31 is selected to provide comfortable support when a patient is seated for extended periods of time. A seat having, for example, an approximate length of 11 inches and a maximum width of 15 inches was found to provide adequate comfort for treating the majority of adults. Optionally, seats of varying size and shape may be used to accommodate patients of varying height and weight.

Cantle 33 comfortably locates and supports the buttocks of the patient in a predetermined position. Pommel 35 extends substantially between the patient's legs to provide pelvic support and to center the patient at the hips about an axis of symmetry through seat 31. Together, pommel 35 and cantle 33 accurately and reproducibly locate the patient on seat 31 during repeated treatment sessions. Seat 31 may be constructed of any number of various materials, including metal and a variety of readily available plastics. Optional padding may be used to improve comfort during long treatment sessions. A preferred embodiment utilizes a standard plastic covered, padded metal bicycle seat.

Base support 37 may be securely attached to the under-side of seat 31 via bolt 39 inserted through base plate 41 and engaging a mounting post 43, to provide rigid support to seat 31. Alternatively a variety of fastening devices, well known in the art, may be used to secure seat 31 to base support 37. Although base support 37 is shown to be detachable from seat 31, it may also be formed integrally with, or otherwise permanently attached to, seat 31. A plurality of linear bearings 45 are attachable to the underside of base plate 41 via screws 47. Each linear bearing 45 slidably engages one of corresponding cross-beam support runners 49 to permit axial displacement of base support 37 and seat 31 along cross-beam support runners 49.

In a preferred embodiment, cross-beam support runners 49 are rigidly supported on opposite ends by end brackets 51 to form, in combination with turn screw 53, a central support girder 55. Central support girder 55 is removably attachable to opposing side rails (not shown) of a standard treatment table via hooks 57 formed in end brackets 51. Optional screws 59 are retractably insertable through threaded holes 61 to secure end brackets 51 against the treatment table side rails and to prevent sliding of central support girder 55. Other fastening devices, such as clamps or interlocking pins, may alternatively be used to secure central support girder 55 to the side rails or frame of a standard treatment table. End brackets 51 are preferably interchangeable with other end brackets (not shown) of varying sizes and shapes in order to accommodate attachment to a variety of standard treatment tables and simulators.

Turn screw 53 is rotatably supported between end brackets 51 and engages corresponding internal threads 63 formed in flange 65 to adjust the position of seat 31 along central support girder 55. Flange 65 attaches to base plate 41 via screws 66 or, alternatively, is integrally formed therewith. Crank 67 securely attaches to one end of turn screw 53 so that it may be turned. Alternatively, rotation of turn screw 53 and corresponding adjustment of seat 31 may be accomplished via electric motors or other devices. An optional millimeter scale 69 and indicator 71 allow for recording the position of seat 31 along central support girder 55 so that this position may be accurately duplicated during subsequent treatment sessions. Millimeter scale 69 may, alternatively, be formed integrally with either of cross-beam support runners 49. Seat 31 may also optionally be adjustably mounted on support base 37, using known seat mounting techniques, to provide elevational adjustment of seat 31. A millimeter scale and indicator may similarly be arranged, as described above, for indicating the elevation of seat 31.

FIG. 3 is a partially disassembled perspective view of a frame in accordance with the present invention. The frame may be used to support various positioning and immobilization devices as needed for immobilizing various anatomical regions of a patient seated upright on a seat assembly as shown in FIG. 2 or, alternatively, on a standard radiotherapy treatment table. The frame includes a rack 91 having a cross-beam support yoke 93 supported at either end by adjustable shanks 95. Cross-beam support yoke 93 is constructed of a central support tube 97, having a preselected diameter, and laterally extending tubes 99, having selectably smaller diameters, which slidably engage central support tube 97. Extension tubes 99 have formed therein a series of axially spaced holes 101 corresponding to holes 103 formed in opposite ends of central support tube 97. The length of cross-beam support yoke 93 is adjusted by sliding extension tubes 99 in or out of central support tube 97 and inserting pins 105 through holes 103 and into one of corresponding holes 101. Elbow sections 107 connect cross-beam support yoke 93 to shanks 95 and may be set in place using a friction fit, an epoxy adhesive or other means.

Shanks 95 are each constructed of a larger diameter tube 109 which slidably engages a smaller diameter tube 111. At least one of tubes 109 or 111 has formed therein a series of axially spaced holes 113, the other tube having a corresponding hole 115 through which pin 117 may be inserted to achieve various length shanks 95. Optionally, one of tubes 109 or 111 may include markings (not shown) indicating the length of shanks 95 so that the set up may be reproduced during subsequent treatment sessions. Slide collars 119 attach to the base of each shank 95 to slidably support rack 91 in a substantially vertical orientation on a pair of cross-beam support runners 121. Pins 123 may be inserted through holes 125 and one of a corresponding series of axially spaced holes 127 formed in cross-beam support runners 121 to adjustably position rack 91 along cross-beam support runners 121.

Cross-beam support runners 121 are preferably of tubular construction, each consisting of a generally horizontal transverse runner section 129 supported at opposite ends by fore and aft legs 131 and 133, respectively. Each of these legs is adapted to receive a hook attachment 135 for removably attaching cross-beam support runners 121 to the side rails of a standard radiotherapy treatment table (not shown). A variety of different hook attachments 135 may be used to attach cross-beam support runners 121 to a variety of standard treatment and simulation tables. Pins 137 are retractably insertable through holes 139 formed in hook attachments 135 and corresponding holes 141 formed in each of legs 131 or 133 to secure hook attachment 135 in place. Hook attachments 135 are preferably rotatable with respect to fore and aft legs 131 and 133, to allow the frame to be mounted in various orientations between opposing side rails of a standard radiotherapy treatment table, to enable use with AP/PA fields or lateral fields, as needed.

Elbow sections 143 connect transverse runner sections 129 to fore and aft legs 131 and 133. These may be set in place using a friction fit, an epoxy adhesive, or other means. Brace 145, consisting of central tube 147, extension tubes 149, and pins 125 insertable through corresponding holes 153 and 155 formed in tubes 147 and 149, respectively, adds rigidity to the frame as shown. The elements of brace 145 are constructed and operate substantially the same as corresponding elements described in connection with cross-beam support yoke 93.

Optional head support 157 is attachable to cross-beam support yoke 93 by brackets 159, for supporting a patient's head in a stable and reproducible position during treatment. Head support 157 includes, for example, a generally rectangular lucite plate 161, in which may be mounted a centrally disposed support pad 163. Attaching and immobilizing features, such as clips and tie-downs, 165 may be added, as needed, to enable attachment of selected thermoplastic immobilization devices for restraining the patient's head during treatment.

The frame is preferably constructed substantially of light-weight materials such as polyvinyl chloride tubing. For improved durability, hook attachments 135 are preferably constructed of a lightweight metal, such as aluminum, or a lightweight metal alloy. Alternatively, the frame may be constructed substantially entirely or in part of lightweight metal alloy tubing. Radiotranslucent materials, such as "PERSPEX" tubing, may also be used to improve patient accessibility. Moreover, it is envisioned that one or more components of the frame as shown in FIG. 3 may be permanently bonded to one another using an epoxy adhesive or other bonding means, or that various mating components may be integrally formed. Alternatively, the entire frame may be of unitary construction.

FIG. 4 illustrates an optional support adaptor for supporting seat assembly 1 along the axis of elongation of treatment table 3 for treating a patient with lateral fields. The support adaptor includes opposing cross-girders 171 attached to one another at a predetermined distance by connecting rods 173. Attachment bar sections 175 allow for removable attachment of seat assembly 1, as shown.

Cross-girders 171 have, formed on each end, U-shaped brackets 179 for removable attachment, via hooks 181, to siderails 7 and 9. Hooks 181 function substantially the same as corresponding hooks 57 discussed in connection with FIG. 2. U-shaped brackets 179 are preferably designed to provide sufficient clearance between cross-girders 171 and the frame of treatment table 3 to maintain attachment bar sections 175 at an elevation comparable to that of side bars 7 and 9 of table 3. This ensures that seat assembly 1 and attached seat 31 will remain at approximately the same height whether mounted in the support adaptor, as shown, or between side bars 7 and 9 as illustrated in FIG. 1. Alternatively, additional attachment bars 177 may be included for supporting seat assembly 1 at a lower elevation, for convenient treatment of head and neck area tumors.

The support adaptor is preferably constructed of a lightweight metal such as aluminum, or a lightweight alloy, so that it may be easily handled by a single radiotherapy technologist. The various components may be assembled using threaded fasteners or any other suitable fastening means. Alternatively, various combinations of components may be formed integrally using known machining and manufacturing techniques.

Optionally, additional frame support rails 183 and 184 may be mounted to U-shaped brackets 179 via spacers 185 so that frame 13 may be mounted on frame support rails 183 and 184 along the axis of elongation of table 3 for treatment of a patient with lateral fields. The distance between optional frame support rails 183 and 184 is, preferably, selected to provide a patient with adequate clearance from frame 13 when supported on seat assembly 1. Side rails 7 and 9 of treatment table 3 may otherwise be too narrow for frame 13 to be mounted in this orientation.

FIG. 5 illustrates use of a radiotherapy treatment chair according to the present invention. After the malignant tumor is located and its approximate size and shape determined, the patient is supported substantially in a straddled stance, as shown, with the legs extending substantially downward from the pelvis. This provides excellent access to the patient for simulation and therapy, particularly to the pelvic cavity and lower abdominal cavity. If required, the patient's head may be supported by an optional bite-block apparatus 201 rigidly mounted to frame 13, as shown, using conventional clamping techniques. Optional adjustable handgrips 15 attach to the shank portions of frame 13 for supporting the patient's hands and arms during treatment.

Treatment is accomplished by first marking the malignant tissue to be irradiated and then adjusting table 3 translationally in the X-Y-Z directions until the tumor is located substantially at the isocenter of radiation source 11. Table 3 and radiation source 11 are then isocentrically rotated to achieve selected radiation entry and exit points through the tumor and the patient's body. An appropriate field size is selected to adequately cover the malignant tissue without exposing too much healthy tissue to the radiation field. Field size may be adjusted either with a standard field aperture or, for individually tailored fields, by using customized shields as are well-known in the art. Preferably, the treatment fields are verified using the treatment machine or a radiographic or other type of simulator to ensure proper size and alignment. The malignant area is then exposed to an appropriate dosage of therapeutic radiation from radiation source 11. Optionally, multiple fields may be directed at the same malignant tumor from various angles to achieve an appropriate level of dose distribution through the tumor, where the multiple fields intersect, while minimizing the dosage level received in surrounding healthy tissue. A treatment planning computer may be used to accurately calculate the precise dose distribution for multiple field exposures.

A combination of multiple malignancies present in the head, neck, upper torso, abdominal and pelvic cavities, and some lower extremities may be treated using a single setup as shown in FIG. 5. Successive tumor sites are moved into the isocenter of radiation source 11 by translational and rotational movement of table 3. If it is necessary to treat adjacent areas, such as head and neck or abdomen and pelvis, the radiation fields can be matched to prevent overdoses of radiation in normal structures and underdoses of radiation in the targeted tumors. Field matching is possible in adjacent areas because the patient receives treatment to both areas while supported in the same straddled stance. This prevents changes in a patient's anatomy that would otherwise make accurate field matching impossible.

It is envisioned that the method described herein in connection with FIG. 5, for treating various malignant tumors disposed throughout a patient's body, may be practiced without necessarily using the particular seat assembly shown in FIG. 2 or the frame shown in FIG. 3. Likewise, although the frame herein described in connection with FIG. 3 is particularly suited for use with a seat assembly as depicted in FIG. it may alternatively be used independently of the seat assembly or with various other seating devices.

Further modifications and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. A radiotherapy treatment chair, for use with a standard, open-couch type radiotherapy treatment table having a detachable section, for supporting a patient in a stable upright position while being treated with therapeutic radiation, comprising:
   a) a horizontal central support girder adapted to span an aperture formed by removing the detachable section from the treatment table;
   b) a saddle-like seat mounted on the central support girder; and
   c) means for removably attaching the central support girder to opposing side rails forming the periphery of the aperture in the treatment table so that the patient may be stably supported on the seat within the aperture.

2. The radiotherapy treatment chair of claim 1 wherein the seat slidably engages the central support girder.

3. The radiotherapy treatment chair of claim 1 wherein the attaching means is adapted to be adjustable such that the girder can be used with a plurality of standard treatment tables.

4. The radiotherapy treatment chair of claim 1 further comprising a frame mounted on the treatment table and adapted to support selected immobilization devices for supporting and substantially immobilizing selected anatomical regions of the patient's body during treatment.

5. The radiotherapy treatment chair of claim 1 further comprising a support adapter comprising two attachment bars supported between the side rails of a standard radiotherapy treatment table, and adapted to accept the attaching means, such that the support girder can be supported between the attachment bars and substantially parallel to the side rails.

6. The radiotherapy treatment chair of claim 5 further comprising a frame support rail mounted parallel to and laterally outwardly spaced from a side rail of the treatment table and adapted to support a frame for supporting and immobilizing the patient.

7. A radiotherapy treatment chair, for use with a standard, open-couch type radiotherapy treatment table having a detachable section, for supporting a patient in a stable upright position while being treated with therapeutic radiation, comprising:
   a) a horizontal central support girder adapted to span an aperture formed by removing the detachable section from the treatment table; and
   b) a saddle-like seat assembly mounted on the central support girder;
   c) means for removably attaching the central support girder between opposing side rails forming the periphery of the aperture in the treatment table so that the patient may be stably supported on the seat within the aperture; and
   d) means for adjusting the position of the seat along the length of the support girder.

8. The radiotherapy treatment chair of claim 7 wherein the seat slidably engages the central support girder.

9. The radiotherapy treatment chair of claim 7 wherein the attaching means is adapted to permit attachment of the girder to any of a plurality of standard treatment tables.

10. The radiotherapy treatment chair of claim 7 wherein the adjusting means comprises a threaded hole in the seat assembly, and a turn screw operatively engaging the hole, the turn screw being rotatable to provide precision adjustment of the position of the seat along the central support girder.

11. The radiotherapy treatment chair of claim 10 wherein the adjusting means further comprises a crank operably attached to the turn screw.

12. The radiotherapy treatment chair of claim 10 wherein the adjusting means further comprises an electric motor operably attached to the turn screw.

13. The radiotherapy treatment chair of claim 7 further comprising a frame mounted on the treatment table and adapted to support selected immobilization devices for supporting and substantially immobilizing selected anatomical regions of the patient's body during treatment.

14. The radiotherapy treatment chair of claim 7 further comprising a support adapter comprising two attachment bars supported between the side rails of a standard radiotherapy treatment table, and adapted to accept the attaching means, such that the support girder can be supported between the attachment bars and substantially parallel to the side rails.

15. The radiotherapy treatment chair of claim 14 further comprising a frame support rail mounted parallel to and laterally outwardly spaced from a side rail of the treatment table and adapted to support a frame for supporting and immobilizing the patient.

16. A frame, adapted for attachment to opposing side rails of a standard radiotherapy treatment table, for supporting a patient in a stable upright position while being treated with therapeutic radiation, comprising:

a pair of laterally spaced support runners, each spanning the space between the side rails and being removably attachable to the side rails of the treatment table; and a rack adapted to rigidly support selected immobilization and support devices for substantially immobilizing selected anatomical regions of the patient's body, the rack comprising laterally spaced shanks attached to and extending generally upwardly from each support runner, and a support yoke attached to and extending between the upper ends of the shanks.

17. The frame of claim 16, further comprising a brace extending between the support runners and rigidly attachable to the support runners.

18. The frame of claim 16, wherein the shanks are slidably attached to the support runners and adapted to be selectively fixed in a preselected position.

19. The frame of claim 16 wherein the frame is constructed substantially of metal tubing.

20. The frame of claim 16 wherein the frame is constructed substantially of polyvinyl chloride tubing.

21. The frame of claim 16 wherein the shanks are adapted to permit adjustment of their lengths and to be fixed at a selected length, such that the height of the frame may be selectively adjusted.

22. The frame of claim 16 further comprising hand grips removably attachable to the shanks.

23. The frame of claim 16 further comprising means attachable to the rack for supporting and immobilizing a patient's head during treatment.

24. The frame of claim 23, wherein the head supporting means comprises a bite block.

25. The frame of claim 16, wherein the runners are adapted to be adjustable in length, and wherein the runners are adapted to be attachable to the side rails of a number of standard radiotherapy treatment tables.

26. The frame of claim 16, wherein the yoke is adapted to be adjustable in length and to be fixed at a selected length, such that the width of the frame may be selectively adjusted.

27. The frame of claim 17, wherein the yoke and the brace are adapted to be adjustable in length and to be fixed at a selected length, such that the width of the frame may be selectively adjusted.

28. A method of radiotherapy treatment for treating a malignant tumor present in a patient's head, neck, upper torso, abdominal or pelvic cavity, comprising the steps of:

a) providing a radiotherapy treatment chair adapted for use with a standard, open-couch type radiotherapy treatment table having a detachable section, comprising a horizontal central support girder adapted to span an aperture formed by removing the detachable section from the treatment table; a saddle-like seat mounted on the central support girder; and means for removably attaching the central support girder to opposing side rails forming the periphery of the aperture in the treatment table so that the patient may be stably supported on the seat within the aperture;

b) supporting the patient in the chair in a straddled stance with the patient's legs extending downward from the pelvis and the patient's head, neck, and upper torso, remaining upright and substantially unobstructed by any supporting structure;

c) providing a frame around the patient and substantially immobilizing the patient, using a selected combination of support and immobilization devices mounted on the frame, to prevent undesirable movement during the treatment; and d) exposing the malignant tumor to a predetermined dosage of therapeutic radiation.

29. A method of radiotherapy treatment for treating patients having a combination of multiple malignant tumors involving areas of the head, neck, upper torso, abdominal or pelvic cavities, comprising the steps of:

a) providing a radiotherapy treatment chair adapted for use with a standard, open-couch type radiotherapy treatment table having a detachable section, comprising a horizontal central support girder adapted to span an aperture formed by removing the detachable section from the treatment table; a saddle-like seat mounted on the central support girder; and means for removably attaching the central support girder to opposing side rails forming the periphery of the aperture in the treatment table so that the patient may be stably supported on the seat within the aperture;

b) supporting the patient in the chair in a straddled stance with the patient's legs extending downward from the pelvis and the patient's head, neck, and upper torso, remaining upright and substantially unobstructed by any supporting structure;

c) providing a frame around the patient and substantially immobilizing the patient, using a selected combination of support and immobilization devices mounted on the frame, to prevent undesirable movement during the treatment; and d) exposing each of the malignant tumors, in succession, to a predetermined dosage of therapeutic radiation.

* * * * *